United States Patent [19]

Schlünken

[11] Patent Number: 4,795,646

[45] Date of Patent: Jan. 3, 1989

[54] PROCESS FOR THE PREPARATION OF BINDER-FREE, TABLETTABLE GRANULES OF CELIPROLOL HYDROCHLORIDE

[75] Inventor: Heinrich Schlünken, Linz, Austria

[73] Assignee: CL Pharma Aktiengesellschaft, Linz, Austria

[21] Appl. No.: 110,810

[22] Filed: Oct. 21, 1987

[30] Foreign Application Priority Data

Oct. 24, 1986 [DE] Fed. Rep. of Germany ....... 3636209

[51] Int. Cl.$^4$ .................. A61K 9/14; A61K 31/17
[52] U.S. Cl. .................. 424/489; 514/597; 514/951
[58] Field of Search .............. 424/489; 514/597, 951, 514/952

[56] References Cited

U.S. PATENT DOCUMENTS

| | | | |
|---|---|---|---|
| 3,784,708 | 1/1974 | Ranucci et al. | 514/951 |
| 4,009,280 | 2/1977 | Macarthur et al. | 514/951 |
| 4,034,009 | 7/1977 | Zolss et al. | 260/553 A |
| 4,161,516 | 7/1979 | Bell | 424/14 |
| 4,372,968 | 2/1983 | Kitamori et al. | 424/280 |
| 4,439,453 | 3/1984 | Vogel | 424/324 |
| 4,470,965 | 9/1984 | Wolf et al. | 424/80 |

FOREIGN PATENT DOCUMENTS

| | | |
|---|---|---|
| 1072569 | 1/1986 | Canada . |
| 852068 | 11/1985 | South Africa . |
| 1142046 | 2/1962 | United Kingdom . |
| 1289996 | 9/1972 | United Kingdom . |

*Primary Examiner*—Paul Lieberman
*Assistant Examiner*—Hoa Van Le
*Attorney, Agent, or Firm*—Mark Dryer

[57] ABSTRACT

Process for the preparation of binder-free granules which can be compressed to give solid medicament forms, which consists in initially placing a predetermined amount of celiprolol hydrochloride, over 50% of which have a particle size below 40 μm and not more than 10% have a particle size above 100 μm, in a fluidized bed granulator, forming a fluidized bed by passing in additional air at a temperature not higher than 30° C. and, by spraying distilled water into the fluidized bed preparing free-flowing granules having a water content of 20–40% by weight, less than 10% of which have a particle size below 63 μm, and drying these granules at temperatures from 30° to 60° C. after they have been discharged, and the use thereof.

8 Claims, No Drawings

PROCESS FOR THE PREPARATION OF BINDER-FREE, TABLETTABLE GRANULES OF CELIPROLOL HYDROCHLORIDE

The invention relates to a fluidized bed process for obtaining tablettable, binder-free granules of celiprolol hydrochloride and to the use of granules prepared by this process for the preparation of solid medicament forms containing celiprolol hydrochloride.

Celiprolol hydrochloride (3-(3-acetyl-4-(3-tert.-butylamino-2-hydroxypropoxy)-phenyl)-1,1-diethylurea hydrochloride), a beta-blocker for the treatment of various heart diseases which is used in human medicine and is particularly reliable, can be prepared, for example, in accordance with U.S. Pat. No. 4,034,009 or EPA 155,518 and, for oral administration, is preferably administered in the form of tablets.

After being synthesized, celiprolol hydrochloride is usually in the form of a very fine powder, over 50% of which has a particle size below 40 $\mu$m, the powder being entirely lacking in free-flowing properties. This powder is therefore not suitable for direct tabletting.

Since celiprolol hydrochloride must be administered in relatively large doses when taken orally, the possibilities of obtaining directly tablettable powder mixtures by mixing the powder with fairly large amounts of auxiliaries, such as flow regulators, are limited, since medicament forms thus prepared are too voluminous and are therefore not suitable, or of only limited suitability, for oral administration.

In order to overcome these difficulties, celiprolol hydrochloride is processed at the present time to give compressible granules, for example by moist granulation using collidone as binder. The disadvantage in this method is that, as a result of the high binder content required to achieve acceptable disintegration times, it is necessary to add fairly large amounts of disintegrators, such as formalin-casein or Ac-Di-Sol (crosslinked sodium carboxymethylcellulose). Toxicological objections to formalin-casein have, however, arisen in recent times and Ac-Di-Sol can result in discoloration of the surface of the tablets.

It is already known that moist granulation can be carried out in a fluidized bed by means of a binder. U.S. Pat. No. 4,372,968 describes a process in which a binder solution is sprayed onto the fluidized active compound (L-ascorbate) at fluidized bed temperatures of up to 80° C., with the formation of tablettable granules. Application of this process to celiprolol hydrochloride has proved impossible for use, since, on the one hand, the use of binders has once more resulted in the disadvantages described above and, on the other hand, it has been necessary to note that the fluidized bed collapses at fairly high temperatures, which has resulted in the fluidized bed material caking firmly on the wall of the fluidized bed granulator. Drying celiprolol hydrochloride in a fluidized bed is also not possible for this reason.

It has now been found, surprisingly, that celiprolol hydrochloride powder can be converted by means of a fluidized bed process into completely binder-free granules which can be compressed to give tablets having excellent properties, if the agglomeration is carried out at low temperatures by spraying in water, without the addition of a binder, and if the resulting granules are dried after being removed from the fluidized bed.

The invention accordingly relates to a process for the preparation of binder-free granules of celiprolol hydrochloride which can be compressed to give solid medicament forms, which consists in initially placing a predetermined amount of celiprolol hydrochloride, over 50% of which have a particle size below 40 $\mu$m and not more than 10% have a particle size above 100 $\mu$m, in a fluidized bed granulator, forming a fluidized bed by passing in additional air at a temperature not higher than 30° C. and, by spraying distilled water into the fluidized bed, preparing free-flowing granules having a water content of 20–40% by weight, less than 10% of which have a particle size below 63 $\mu$m, and drying these granules at temperatures from 30° to 60° C. after they have been discharged.

Commercially available fluidized bed granulators are suitable for carrying out the process according to the invention. Such fluidized bed granulators consist essentially of a material container into which the fluidizing gas is passed from the side or from below, it being possible to control both the flow rate and the temperature of the fluidizing gas passed in. These devices are also equipped with one or more spray heads in the form of single-substance or two-substance nozzles through which pure liquids and solutions can be sprayed into the material container at an adjustable spraying rate by means of a pump, and which are so arranged that the atomized liquid or solution flows directly into the fluidized bed. If required, a mechanical stirring or chopping device on the base of the container or a vibrating device should ensure an additional mixing effect.

The fluidizing gas used can, in the simplest manner and with no disadvantage for the quality of the active compound, be air. However, other gases which are inert towards the active substance, such as, for example, nitrogen, are, of course, also suitable instead.

The celiprolol hydrochloride powder used for the granulation, over 50% of which has a particle size less than 50 $\mu$m, should contain not more than 10% of fractions having a particle size over 100 $\mu$m. If it should contain fractions of particle size over 250 $\mu$m, it must be ground before the fluidized bed granulation.

In order to carry out the process in practice, an amount of celiprolol hydrochloride suitable for the particular fluidized bed granulator is initially placed in the material container, a fluidized bed is formed by passing in the fluidizing gas at not higher than 30° C., and water is then sprayed in.

The amount of water to be sprayed in depends on the amount of celiprolol hydrochloride initially taken, on the moisture and temperature of the fluidizing gas, on the duration of the fluidized bed granulation and on the desired water content of the granules. It is so chosen that the moist granules obtained have a water content of about 20–40% by weight, and it amounts to about 20 and 60% by weight of the amount of celiprolol hydrochloride initially taken. The amount of water sprayed in and the temperature of the fluidizing gas, which must not be more than 30° C. but is advantageously at room temperature, are matched with one another in such a way that granules having the properties indicated above are obtained, it being of course necessary to take account of the fraction of the amount of water which evaporates during spraying.

The endpoint of the moistening process is determined by visually observing the agglomeration and by determining the water content of a sample by the K. Fischer method.

In accordance with a preferred embodiment of the present invention, the parameters of the fluidized bed granulation are matched with one another in such a way that the resulting granules have a water content of about 25-30% by weight after being discharged from the fluidized bed granulator. The amount of water sprayed in is preferably 25-35% by weight of the amount of celiprolol hydrochloride initially taken.

When granules having the desired properties have been formed, they are discharged from the fluidized bed granulator continuously or discontinuously and are subjected to moisture screening through a screen having a mesh width of, for example, 2.0 mm.

The moist granules must be dried outside the fluidized bed granulator, since the granules are deposited on the container wall at a temperature above 30° C. and disintegrate once more into a powder below 30° C. Drying can be carried out after discharge from the fluidized bed granulator, with or without vacuum, by any of the methods customary in the production of pharmaceuticals. It is preferable to dry the granules on sheet metal trays at temperatures from 30°-60° C., preferably 38°-40° C. The drying time depends on the temperature and can vary within a certain range. A preferred drying time is 10-20 hours. Granules in which the residual water content does not exceed 2%, relative to the total weight, are obtained in this manner.

The resulting granules contain less than 10% of a fraction having a particle size less than 63 μm. Granules, less than 0.5% of which have a particle size above 1,000 μm and less than 5% have a particle size below 63 μm are obtained in accordance with a preferred embodiment. Granules having the limits mentioned above and in which 70% of the fraction have a particle size between 160 and 800 μm are particularly preferred.

The advantages of the present process lie in the simplicity of the process and in the increase in the product quality of the granules obtained. The use of water instead of a granulating liquid containing binder results in granules consisting of pure active substance, it being, surprisingly, possible to avoid the use of binders, which has proved unfavorable. These granules can be compressed either direct or, if appropriate, after the addition of further pharmaceutically tolerable auxiliaries or active compounds, to give solid medicament forms having excellent pharmaceutical properties, such as high mechanical strength and low disintegration time, without the need for anxiety regarding interaction between a binder and active compounds and auxiliaries.

Solid medicament forms of this type embrace compacts of every size and shape, such as tablets, coated tablets, tablet and coated tablet cores, multi-layer tablets or very small compressed tablets intended for filling into hard or soft gelatine capsules, and the like. These medicament forms can be provided with the customary protective coverings and coatings and can contain substances for improving the taste.

Example:

5,000 g of celiprolol hydrochloride are initially placed in a fluidized bed granulator (WSG 5 made by Glatt, Germany). The fluidized bed is formed by passing in air at room temperature (15°-25° C). 1,500 ml of distilled water are sprayed in by means of a hose pump at a spraying rate of approx. 70 ml/minute until visible agglomeration sets in.

The vibrating device is switched on for 30 seconds every 2 minutes.

The start of the formation of agglomerates can be discerned by visual observation after 30 minutes. According to experience, this is the best time at which to discontinue fluidized bed granulation. The moist granules have a water content of 29% by weight after being discharged from the fluidized bed granulator.

After moist screening on a Frewitt screening machine through a screen having a mesh width of 2.0 mm, the granules are dried for 15 hours at a temperature of 39° C. on sheet metal trays in a drying cabinet. The residual water content is then 1.6%.

An examination of particle size distribution gave the following figures:

| | |
|---|---|
| Over 1,000 μm | —% |
| 800 μm-1,000 μm | 1.5% |
| 500 μm-800 μm | 22.3% |
| 250 μm-500 μm | 35.3% |
| 160 μm-250 μm | 20.7% |
| 100 μm-160 μm | 10.7% |
| 63 μm-100 μm | 5.9% |
| below 63 μm | 3.6% |

The granules have excellent free-flowing properties.
What I claim is:

1. Process for the preparation of binder-free granules of celiprolol hydrochloride which can be compressed to give solid medicament forms, characterized in that a predetermined amount of celiprolol hydrochloride, over 50% of which have a particle size below 40 μm and not more than 10% have a particle size above 100 μm is initially placed in fluidized bed granulator, a fluidized bed is formed by passing in additional air at a temperature not higher than 30° C. and, by spraying distilled water into the fluidized bed, free-flowing granules having a water content of 20-40% by weight and less than 10% of which have a particle size below 63 μm are prepared and these granules are dried at temperatures from 30° to 60° C. after they have been discharged.

2. Process according to claim 1, characterized in that the free-flowing granules have a water content of 25-30% by weight before being dried.

3. Process according to claim 1, characterized in that the amount of distilled water sprayed in is 20 to 60% by weight of the amount of celiprolol hydrochloride initially taken.

4. Process according to claim 3, characterized in that the amount of distilled water sprayed in is 25-35% by weight of the amount of celiprolol hydrochloride initially taken.

5. Process according to claim 1, characterized in that granules in which less than 0.5% have a particle size above 1,000 μm and less than 5% have a particle size below 63 μm are formed.

6. Process according to claim 1, characterized in that granules in which 70% of the fraction have a particle size between 160 and 800 μm are formed.

7. Process according to claim 1, characterized in that the granules are dried to a residual water content of less than 2% by weight.

8. Process according to claim 1, characterized in that the granules are dried for 10-20 hours at temperatures of 38°-40° C. in a drying cabinet.

* * * * *